United States Patent
Van Den Elshout et al.

(10) Patent No.: US 10,357,523 B2
(45) Date of Patent: Jul. 23, 2019

(54) ANIMAL FEED COMPRISING GRAIN AND AGARICUS BLAZEI EXTRACT AND USE OF THE FEED MATERIAL

(71) Applicants: Wilhelmus Hubertus Henricus Antonius Van Den Elshout, Venlo (NL); Pierre Michel Grammare, Lakanal (FR); SSIPfeed B.V., Venlo (NL)

(72) Inventors: Wilhelmus Hubertus Henricus Antonius Van Den Elshout, Venlo (NL); Pierre Michel Grammare, Lakanal (FR)

(73) Assignee: SSIPFEED B.V., Venlo (NL)

( * ) Notice: Subject to any disclaimer, the term of this patent is extended or adjusted under 35 U.S.C. 154(b) by 846 days.

(21) Appl. No.: 14/400,337

(22) PCT Filed: May 14, 2013

(86) PCT No.: PCT/EP2013/059903
§ 371 (c)(1),
(2) Date: Nov. 11, 2014

(87) PCT Pub. No.: WO2013/171194
PCT Pub. Date: Nov. 21, 2013

(65) Prior Publication Data
US 2015/0140098 A1 May 21, 2015

(30) Foreign Application Priority Data
May 14, 2012 (NL) .................................... 2008812

(51) Int. Cl.
| | | |
|---|---|---|
| A23K 10/12 | (2016.01) | |
| A23K 10/30 | (2016.01) | |
| A23K 50/75 | (2016.01) | |
| A61K 36/07 | (2006.01) | |
| A23K 20/163 | (2016.01) | |
| A23K 20/174 | (2016.01) | |
| A61K 31/201 | (2006.01) | |
| A61K 31/07 | (2006.01) | |
| A61K 31/59 | (2006.01) | |
| A61K 31/575 | (2006.01) | |

(52) U.S. Cl.
CPC .............. *A61K 36/07* (2013.01); *A23K 10/12* (2016.05); *A23K 10/30* (2016.05); *A23K 20/163* (2016.05); *A23K 20/174* (2016.05); *A23K 50/75* (2016.05); *A61K 31/07* (2013.01); *A61K 31/201* (2013.01); *A61K 31/575* (2013.01); *A61K 31/59* (2013.01)

(58) Field of Classification Search
CPC ...... A23K 10/12; A23K 10/30; A23K 20/163; A23K 20/174; A23K 50/75; A23K 1/00; A23K 1/18; A61K 31/07; A61K 31/201; A61K 31/575; A61K 31/59; A61K 36/07
See application file for complete search history.

(56) References Cited

U.S. PATENT DOCUMENTS

| 4,204,364 | A | 5/1980 | Maul et al. |
| 2008/0187574 | A1 | 8/2008 | Holliday |

FOREIGN PATENT DOCUMENTS

| CN | 101371683 A | 2/2009 |
| EP | 1714674 A1 | 10/2006 |
| JP | 2004/321033 A | 11/2004 |
| KR | 20050013900 A | * 2/2005 |
| RU | 2097979 C1 | * 12/1997 |
| RU | 2542523 C1 | * 2/2015 |

OTHER PUBLICATIONS

Sanchez, C "Reactive oxygen species and antioxidant properties from mushrooms" Synthetic and Systems Biotechnology 2017, 2, 13-22. DOI:10.1016/j.synbio.2016.12.001.*
Jonathan et al "Effect of physical and chemical factors on mycelial growth of ten wild Nigerian mushrooms during cellulase and amylase production" NPAIJ, 2011, 7(4),p. 211-216.*
Block, SS et al "Experiments with Submerged Culture" Agricultural and Food Chemistry, Sep. 30, 1953, p. 890-893.*
Amerah AM et al "Feed particle size: Implications on the digestion and performance of poultry" World's Poultry Science Journal, 2007, 63,p. 439-455. DOI: 10.1017/S0043933907001560.*
Unicorn Imp & Mfg Corp ("Cultivation of Agaricus blazei" retrieved online <URL:https://unicornbags.com/cultivation/agaricus-blazei>, accessed Sep. 2017 (archived May 2, 2012), 14 pages.*
Ikeya M, et al "The effect of feeding ground Agaricus blazei Murill on egg production in hen", Bull. of Shizuoka Swine and Poultry Exper. Station, The Ag., Forestry and Fisheries Res. Info. Technol. Ctr., AFFRIT, Japan, No. 14, Jan 1, 2003, pp. 29-32,, ISSN: 0914-6520 (Eng. Translation, 12pp.) (Year: 2003).*
Dutch Search Report for priority document NL2008812 dated Feb. 5, 2013.
International Search Report for PCT/EP2013/059903 dated Jun. 28, 2013.
International Preliminary Report on Patentability for PCT/EP2013/059903 dated Nov. 18, 2014.

(Continued)

*Primary Examiner* — Aaron J Kosar
(74) *Attorney, Agent, or Firm* — Ramin Amirsehhi; David P. Owen; Philip Tsai

(57) ABSTRACT

The invention relates to the use of feed material comprising grain and *Agaricus Blazei*, comprising the *Agaricus* species in an amount between 10 to 50% by weight on dry matter, and the feed material having a moisture content of less than 10% (relative to dry matter), for administration to chicken for improvement of egg laying, preferably for improving shell quality and/or for extending the egg laying period. The invention further relates to a process for making the feed material, and feed for laying hens comprising the feed material.

11 Claims, No Drawings

(56) References Cited

OTHER PUBLICATIONS

Ikeya M et al: "The effect of feeding ground Agaricus blazei Murill on egg production in hen", Bulletin of Shizuoka Swine and Poultry Experiment Station, The Agriculture, Forestry and Fisheries Research Information Technology Center, Affrit, Japan, nr. 14, Jan. 1, 2003, pp. 29-32, XP008159889, ISSN: 0914-6520.

Jonathan, Segun G. et al: "Evaluation of Ten Wild Nigerian Mushrooms for Amylase and Cellulase Activities", Mycobiology 39(2): 103-108 (2011).

François, Jean M: "A simple method for quantitative determination of polysaccharides in fungal cell walls", Nature protocals (2007) 1:2995-3000.

* cited by examiner

ANIMAL FEED COMPRISING GRAIN AND AGARICUS BLAZEI EXTRACT AND USE OF THE FEED MATERIAL

CROSS REFERENCE TO RELATED APPLICATION

This application is a 35 U.S.C. 371 National Phase Entry Application from PCT/EP2013/059903, filed May 14, 2013, which claims the benefit of Dutch Patent Application No. 2008812 filed on May 14, 2012, the disclosure of which is incorporated herein in its entirety by reference.

This invention relates to feed material for chicken and other fodder, and more in particular to the use of this feed material for improving long term egg shell quality, and increasing the egg laying period of laying hens.

Chicken and eggs are a widely used as food for human consumption. Large numbers of chicken are grown for egg production. Generally, female chicken (laying hens) are grown for 17 weeks, after which period they can be used for egg production. The growth and maintenance of the laying hens is highly optimized, and currently, the hens are producing eggs for about 60 weeks. Initially, the laying percentage reaches about 95% (>93%) after about 10 weeks, for a period of about 10 weeks, but thereafter the laying percentage decreases. Also, the quality of the egg shells deteriorates on average.

It is an object of the invention to provide a feed, or feed material, that allows an improvement in egg shell quality and/or egg laying period for the laying hens.

The object of the invention is achieved with providing the chickens with a feed or feed material comprising *Agaricus blazei*, wherein the *Agaricus* species is fermented on grain, the fermented grain is dried, and optionally pulverized, and used as feed material. Hence, the present invention relates to a feed material comprising grain and *Agaricus blazei*, comprising the *Agaricus* species in an amount between 10 to 50% by weight on dry matter, and the feed material having a moisture content of less than 10% (relative to dry matter), for administration to chicken for improvement egg laying, preferably for improvement of egg shell quality and/or for extending the egg laying period.

The mushroom species according to the invention is an *Agaricus blazei*, preferably *Agaricus blazei murill* (also called *A. blazei Brasiliensis*, or *Agaricus subrufescens*, or *Agaricus rufotegulis*). At present, it is thought that *Agaricus subrufescens* is the correct name; however, in this application, the more common *Agaricus blazei murill* will be used. Herein below, the abbreviation ABM for *Agaricus blazei murill* is used interchangeably. The preferred *Agaricus* species is *Agaricus blazei murill*.

The use of extracts of *Agaricus blazei* for administration to laying hens, for example an extract in water, as a solution or absorbed on zeolites, is described in JP2004/321033. Some improvement is seen in strengthening the immune system according to this reference. However, JP2004/321033 does not suggest the improvements of the present invention. Further, Ikeya et al. (Bulletin of the Shizuoka swine and poultry experiment station, the agriculture, forestry and fishery research information technology center (AFFRIT), Japan, no 14, 1 Jan. 2003 pp 29-32 (XP008159889, ISSN 0914-6520)) describes the use of ground *Agaricus blazei murill* for laying hens. However, the improvements found in the present invention are neither described, nor suggested therein.

Fermentation of *Agaricus blazei* species on grain is known as such, also for feed applications in general, like for example described in CN101371683. However, the improvements found in the present invention are neither described, nor suggested therein. US2008/187574 describes the fermentation of multiple microorganisms on grain. However, the improvements found in the present invention are neither described, nor suggested therein.

The mushroom species according to the invention, which gives very good results, is an *Agaricus blazei*, preferably *Agaricus blazei murill* (also called *A. blazei Brasiliensis*). Herein below, the abbreviation ABM for *Agaricus blazei murill* will be used interchangeably.

The *Agaricus blazei* fungus is grown as mycelium on a grain source, and harvested as such. Hence, it is not necessary to execute mycelium growth till fruit bodies emerge, nor is it necessary to separate the growth medium from the mycelium. Thereby, the present invention allows for an economically effective way of providing useful feed for chicken resulting in increased egg production. The improvement is seen during the normal egg laying period, but is also clear from improved egg shell, and increased laying period.

As the grain source, several commonly known grain types are useful, such as for example corn, wheat bran, oat, sorghum, barley, whole wheat, rye, soy beans, maize and the like. Mixtures can be used as well. Further, addition of carbon source, ammonia source or the like can be useful to increase growth of the mycelium. Calcium compounds like chalk may be added. Rye or oat are particularly preferred because ABM grows particularly well on these substrates.

In order to obtain a suitable fermented ABM, it is preferred that the grain source comprises a sufficiently high moisture content. A suitable moisture content is between about 10-80% moisture (measured as weight of the moist product minus a dried product, divided by the moist product weight). A preferred moisture content is between about 30 and 70%, like for example about 50%.

The grain source is sterilized before inoculation with the ABM mycelium. Inoculation, and the preparation of the inoculate follows standard techniques, like for example described in U.S. Pat. No. 4,204,364.

The fermentation generally takes place in containers of 20 to 50 liter size, like in bags or trays, like for example 25 or 30 liter bags. Fermentation preferably takes place in a conditioned environment. Generally, the time for fermentation will be between 15 and 75 days, like between 15 and 55 days, preferably between 20 and 45 days. Too short will cause relatively low mycelium content; a too long period is economically less interesting. The temperature during fermentation preferably is between 20 and 35° C., and most preferred between 28 and 30° C. The humidity preferably is between 40% and 90% RH, such as for example 50 or 60% RH.

After a suitable period of fermentation, the amount of mycelium is between about 10 and 50% (on dry weight of the mixture of grain and mycelium), preferably between 20 and 30%. The amount of mycelium can be measured indirectly, for example based on the ergosterol content, as will be further elucidated in the examples. Any suitable method for determining the mycelium content can be used. For example, it is also possible to measure the mycelium content based on the amount of chitin.

After the fermentation, the fermented grain is dried. The moisture content of the dried fermented grain preferably is about 10% or less, preferably about 8% or less and more preferably about 6% or less. A lower moisture content aids in achieving a good storage stability. Generally, the moisture content will be about 2% or more, and preferably about 3% or more. As such, a feed with very low moisture content has no disadvantages from technical perspective, but it is more costly to produce.

Any drying technique may be suitable. A suitable apparatus includes a belt dryer, bulb dryer, tumble dryer or fluid bed dryer. Preferably, the apparatus is such that it is able to perform the drying at reduced pressure. In general, it is preferred that the temperature remains below 100° C. Preferably, the fermented grain is dried by air drying at between 5 and 100° C., preferably between 25 and 90° C., more preferably below 63° C., and even more preferably below 50° C. Drying at a temperature below about 50° C. has the advantage that extra-cellular enzymes, like cellulases keep their activity. In case the enzymes that are of interest have been modified to be resistant to higher temperatures, a higher temperature for drying is preferred because drying speed is increased. If a temperature is chosen below 63° C., 45° C., or in particular at about 35° C. or lower, it is preferred to apply reduced pressure. The low temperature applied during the drying step has the further advantage that heat sensitive compounds produced during fermentation remain in an active form in the feed.

The dried fermented grain is storage stable for several months up to at least one year (e.g. for two years), with little reduction of the nutritive value of the feed material.

The fermented dried grain (feed material) can be used as such, as or in chicken feed.

For improving mixing characteristics with common feedstock, and to allow reproducible administration to the laying hens, it is preferred to crush or mill the fermented dried grain to a particle size ($d_{50}$) between 0.01 and 10 mm, preferably lower than 5 mm, and even more preferably between 0.1 and 3 mm. The particle size range preferably is between 0.1 and 2.0 mm for about 90% or more of the feed material, preferably of about 95% or more of the feed material, and more preferably of about 98% or more of the feed material. As chicken feed, suitable particle grain sizes ($d_{50}$) are for example about 1.0 mm, about 1.2 or about 1.4 mm. Preferably, grain size (absolute) is smaller than 10 mm. In one embodiment, the grain size preferably is smaller than 5 mm, particularly for grown up chicken, and even more preferably smaller than 3 mm, as that is about the maximum size for starter laying hens.

The feed material produced in this way is very suitable as feed material for chicken and other fodder with a crop. Because of the preferred low temperature during drying, extracellular enzymes like cellulases and amylases remain active. Intake by the chicken of such active enzymes aid in feed conversion in the crop.

The present invention also is concerned with a process for producing feed material, comprising
a) fermenting *Agaricus blazei* on grain with a moisture content between 10 and 90%, until 10-50% mycelium content, preferably on rye or oat;
b) drying the fermented grain to a moisture content of between 2 and 8 wt % (with respect to the dry material) at a temperature below 50° C., and preferably between 20 and 45° C. while applying reduced pressure;
c) and milling the so obtained fermented and dried material to a particle size with a $d_{50}$ between 0.01 and 10 mm.

The fermented, dried and optionally milled fermented grain (the feed material) can be used as such as feed, as a separate feed source, or it can be mixed with other common feedstock for chicken. Preferably, the feed material is mixed with the general feedstock, as that allows better standardization and/or reproducibility.

The feed material generally will contain between 10 and 50 wt % of mycelium (based on dry weight), preferably between 20 and 30 wt %. The amount of mycelium can be measured based on the content of ergosterol. The fermentation will cause a number of useful compounds to be present in the fermented grains. The *Agaricus blazei* species produces for example, ergosterol, extra-cellular enzymes like cellulases and amylases, and 1,3- and 1,6-β-glucans.

Ergosterol is a sterol from which vitamin D is produced by the chicken. Hence, the ergosterol—while vitamin D being important for the calcium resorption form the gut—is thought to be instrumental in improvement of the egg shell quality. The amount of ergosterol in the feed material generally will be between 0.05 and 0.5 g ergosterol/kg feed material. Ergosterol can be measured with standard techniques, like HPLC or GC. Preferably, quantitative extraction is performed on pulverized dry fermented grain, which can be done with hot 80% ethanol.

It is preferred to use such an amount of feed material according the invention, that the mixed feed comprises between 50 and 1000 microgram ergosterol per kg feed material, preferably in an amount of 100-600 microgram ergosterol per kg feed material.

The extra-cellular enzymes, that remain active with the current preferred drying process, may aid in an improved feed conversion. The feed material according the present invention preferably comprises active extra-cellular cellulases. The presence of extra-cellular cellulases can be determined according to the methods described in Mycobiology 39(2): 103-108 (2011). In a preferred embodiment, the cellulase activity is between 0.1 and 0.8 unit/ml when 10 gram of material is extracted with 20 ml of water. In this extraction, 10 gr of dry feed material is soaked with 20 ml of water at 20° C. for two hours, and thereafter the water is squeezed out of the mixture in a press, and the enzymatic activity in the extracted water measured.

The 1,3- and 1,6-β-glucans are known to improve the immune system. The glucans are water soluble. The amount of these glucans generally will be between 3 to 100 gram, preferably 6 to 60 gram and most preferable 10 to 40 gram per kg of the feed material (i.e. the fermented grain).

The amount of 1,3- and 1,6-β-glucans in the total feed for chicken will be between 20 and 200 mg/kg feed, preferably between 50 and 100 mg/kg feed. 1,3- and 1,6-β-glucans can be measured with standard kits. However, it appeared that measurement in the fermented grain resulted in unreliable results. Hence, the amount of 1,3- and 1,6-β-glucans in the fermented grains can be determined indirectly, by determining these compounds in pure fermented ABM, and calculating from the % conversion (measured via the amount of ergosterol) the amount of 1,3- and 1,6-μ-glucans.

Some analysis in the fermented grain is complicated because of the components of the grain. It can be useful to determine the production of useful components in pure mycelium. This can be done by growing the mycelia in a fermenter under non-limiting conditions, removing the medium, and measuring the components of the mycelium. Obviously, only intracellular components are measured in this way. The ABM used by the present inventors produced about 10.7 g/kg GlcNac release, as measure for chitin, about 0.65 g/kg mycelium of ergosterol, about 120 g/kg mycelium of 1,3-β-glucans and 1,6-β-glucans.

The amount of mycelium can be measured based on the content of chitin, but also for example based on the amount of ergosterol. The determination while using chitin is preferred, as that is a stable compound (while ergosterol is UV sensitive). When done correctly, both methods should give approximately the same results.

The method used for the determination of conversion via the assessment of amount of chitin is described in Nature protocols (2007) 1:2995-3000. In short, chitin is first liberated from the cell walls, and while using chitinase, chitin is hydrolyzed and N-acetylglucosamine is formed, which can be determined quantitatively with tetraborate and Reissig reagent. The amount found in the fermented grain should be compared with a calibration line made from pure mycelium.

The amount of mycelium (as pure dry matter) given to the laying hens per day, generally will be between 0.1 and 1.0 kg per ton feed, preferably between 0.2 and 0.8 kg per ton feed. The amount of feed material, to be added to the normal feedstock can be adjusted after assessing the amount of mycelium. The amount of feed material generally will be about 0.2 kg per ton or more, preferably about 0.5 kg or more, and more preferably about 1 kg per ton feed or more. Generally, the amount will be about 10 kg per ton feed or less, preferably about 5 kg per ton feed or less. Suitable examples include 2, 3 or 5 kg per ton feed.

A hen consumes initially about 70 gram or more feed per day per kg bodyweight, and after a few weeks about 100 up to 125 gram of feed per day.

The amount of feed material (25% conversion on rye) according to the invention given per laying hen is between about 20 and 500 milligram per kg chicken-bodyweight per day, preferably between 50 and 300 milligram per kg chicken-bodyweight per day, like for example about 100, about 150, or about 200 milligram/chicken-bodyweight/day.

In view of the small amounts, the feed material according the present invention preferably is mixed with other feed components. Common feedstock for chicken are grains, soybean meal, sesame meal, fish meal, cottonseed meal and the like. Preferably, the feedstock comprises more than 15 wt %, like for example between 15 and 23 wt % protein and a sufficient amount of energy. Furthermore, preferably the feedstock comprises calcium, in an amount of about 2 wt % or more, preferably about 3 wt % or more, and more preferably about 4 wt % or more. The feedstock preferably also comprises about 1-2 wt % linoleic acid (preferably as glycerol ester). Additionally, the feed preferably comprises vitamins like vitamin A (preferably more than 10000 IU), vitamin D (preferably more than 2000 IU) and a sufficient amount of biotin, cholin, antioxidants, manganese, zinc, and trace materials. If the feed material according to the present invention is used, the amount of vitamin D may be lower. Generally, the feed for chicken varies over the laying period. The feed generally contains preferably more than 15 wt % protein, more than 2 wt % calcium and more than 1 wt % linoleic acid.

It is not necessary to use the feed material of the present invention every day. Intermittent administration, like for example every other day, once every three days, or once a week may be suitable as well. It is thought that every day, or every other day is most effective.

In one embodiment of the invention, the feed material is used during the whole of the growth and egg laying period. Using the feed material during the whole of the period has the advantage that mortality in the initial phase of growth is reduced, which leads to an increase in egg production for a given group of hens.

In another embodiment, the feed material is used only during the second half of the laying period of the laying hens. In this embodiment, the feed material is used only (or predominantly only; incidental use before that period is of course immaterial) from about week 30 onwards of the egg laying period or later, and preferably from about week 40 onwards, and most preferably from week 45 onwards of the egg laying period. The feed material should however at least be used from about week 50 onwards, otherwise reduced improvement will be observed. This embodiment has the advantage of reduced use of feed material, while still a very effective increase of egg laying period with good egg shell quality is observed.

The present invention will be elucidated with the following examples, without being limited thereto.

EXAMPLES

Feed Material

Feed material was produced as follows. Bags of 15 L with 3 kg wet rye (50% moisture) were inoculated with about 80 mg ABM mycelium and cultivated for 42 days at 28° C. at 50% humidity. The product was dried (to a moisture content of less than 5%) with a vacuum rotary vapor drum at 35° C. at 20 mmHg pressure. The dried material was coarsely milled at $d_{50}$ 1000 micron (1 mm).

The bioconversion was indirectly measured via the ergosterol amount. The method was as follows: The samples were lyophilized for 48 hours before extraction. Ergosterol was extracted in the dark from 100 mg of biological material (mushroom or vegetable matrix) in 15 ml of KOH/MeOH (1:10, w/v) for 1 h at 80° C. and then rapidly cooled in ice. 30 µg of internal standard (cholesterol: 1 mg/l in hexane) are added prior extraction. After adding 2 ml of water, an extraction is performed twice with 4 mL of hexane. The organic layers were collected and evaporated under nitrogen flow. Ergosterol was analyzed by gas chromatography (FID detector, column DB-5). The amount of ergosterol in 100% ABM is for this strain 0.65 g/kg.

The ergosterol and glucan content of the feed material is reported in Table 1; amounts are values of the feed material (the fermented and dried grain). The amount of glucans was measured in submerged fermented ABM, and measured in accordance with AACC method 32-23 (McClearly method), as for example described by Megazyme (Wicklow, Ireland). The amount in the feed material was calculated based on the conversion determined via the ergosterol content.

TABLE 1

| Run | Fermentation % (bioconversion) | Ergosterol | 1,3-1,6-β-glucan |
|---|---|---|---|
| 1 (oat) | 25% in 42 days | 0.16 g/kg | 30.2 g/kg |
| 2 (oat) | 18% in 35 days | 0.12 g/kg | 21.8 g/kg |
| 3 (rye) | 35% in 35 days | 0.23 g/kg | 42.4 g/kg |

Trial with Laying Hens

A large scale trial was set up, with two groups of laying hens (Lohmann Bruin Lite) of 17 week old in exactly the same buildings. The groups consisted of 10000 and 11000 laying hens respectively. The group of 11000 hens were treated whereas the other group was used as a control. The management for the two groups were the same (temperature, water, feed, air treatment etc.). For the treated group 3 kg fermented oat (20% bioconversion; i.e. 20% by weight mycelium) per ton feed was added by an automated dosing unit (WAM Holland). All the feed for the treated group was enriched with the ABM feed material. The standard feed consisted of standard optimized feed for laying hens. This type of feed is adapted to the laying hens over the period of egg production.

Results

Although some variations were observed during the trial with respect to egg laying performance, the treated group overall produced about 3% more eggs on the same amount of feed (in g/egg). The maximum egg laying period (>93%) was about 12 weeks in the control. In the treated group, >93% of good quality eggs was achieved from week 31 up to a at least 60 weeks; so for more than 30 weeks.

The 75% performance parameter (where 75 out of 100 chicken lay on the average 1 egg a day) was reached after 60 weeks egg laying (total life span 77 weeks) for the control group. The 75% figure for the treated group was at 67 weeks (84 weeks total life span). So next to the 3% increase during the "normal" period, the treated laying hens produced 350,000 eggs more in the additional 7 weeks before slaughter (i.e. more than additional 30 eggs per hen, leading to an average increase of about 20% in number of eggs produced per hen). The overall mortality was about ¼$^{th}$ lower in the treated group than in the control groups.

The ABM feed material was added over the complete period i.e. 165 gram ABM feed material for the treated group in 67 weeks.

Total egg production over the 60 week egg laying period is given in table 2:

TABLE 2

| Stable | Birds start | Birds average | Eggs | Average number of eggs per bird |
|---|---|---|---|---|
| 1 (control) | 10,000 birds | 9,800 birds | 3,498,600 | 357 |
| 2 (treated) | 11,000 birds | 10,835 birds | 4,225,650 | 390 | the average quality and weight of the eggs were essentially the same for the two groups through a large part of the trial. The egg shells in the treated group appear to be thicker at the end of the laying period. The quality of the eggs in the treated group allow for egg production up to 67 weeks, also because the egg-shell is of sufficient quality.

Further Feed Material

Further feed material was produced in a comparable manner. The bioconversion was indirectly measured via the chitin amount as described in Nature protocols 1, 2995-3000, 2007. The grain used does not comprise chitin, so all chitin measured originates from the mycelium. The conversion can be calculated via the amount of formed GlcNac, and its absorbance at 585 nm. Per mg of dry fungal mass, the amount of GlcNac is 1.06% (standard deviation, 0.2%). Hence, the OD measured for an amount of GlcNac obtained from 10 mg of pure dry mycelium is 0.93. Hence, for a measured OD (ODm), dividing the ODm by 0.093, gives the amount of mycelium. This amount, multiplied by 100, and divided by the initial amount of mycelium for a given sample gives the percentage bioconversion. The feed material, produced on rye showed a bioconversion of 26% in 70 days. The amount of ergosterol was 0.17 g/kg and the amount of β-glucans was 31 g/kg.

Trial with Laying Hens During Part of the Egg Laying Period

In a further trial, feed material was used only from week 41 onwards, hence during the last 20 weeks of the egg laying period of untreated hens. The amount used was twice the amount given in the former trial (hence, 5 kg of the product with 26% bioconversion) mixed with the normal feed for laying hens as described in the example above. The egg laying period was extended with 5 weeks till the threshold value of 75% was reached, with eggs with sufficient egg shell quality.

The invention claimed is:

1. A process for producing a feed material, consisting of:
    a) fermenting mycelium of *Agaricus blazei* fungus on an amount of grain, wherein the moisture content by weight of the grain is between 10 wt % and 90 wt %, until the fermented grain comprises by dry weight thereof 15 wt % to 50 wt % mycelium content,
    b) drying the fermented grain at a temperature between 25° C. and 90° C. and to reduce the moisture content thereof of less than 10 wt %, and
    c) milling the so obtained fermented and dried material to a particle size with a d$_{50}$ between 0.01 mm and 10 mm thereby producing said feed material.

2. The process according to claim 1, wherein the grain is rye or oat.

3. The process according to claim 1, wherein the dried material has a particle size with a d$_{50}$ between 0.01 mm and 3 mm.

4. The process according to claim 1, wherein the drying temperature is below 50° C.

5. The process according to claim 1, wherein the feed material has a moisture content between 2 wt % and 8 wt %.

6. The process according to claim 1, wherein the feed material has a particle size with a d$_{50}$ between 0.01 mm and 3 mm.

7. The process according to claim 1, wherein the feed material comprises ergosterol in an amount of 100 mg and 600 mg per kg feed material.

8. The process according to claim 1, wherein the feed material comprises active cellulases having an activity between 0.1 to 0.8 unit/ml in an extract which is obtained if 10 g feed material is extracted with 20 ml water.

9. The process according to claim 1, wherein the feed material comprises an amount of 1,3- and 1,6-β-glucans of between 3 g and 100 g, per kg of the feed material.

10. The process according to claim 1, wherein the feed, per kg thereof, comprises:
    an amount of ergosterol of 100 mg to 600 mg, and an amount of 1,3- and 1,6-β-glucans of between 3 g and 100 g per kg of the feed material.

11. The process according to claim 1, wherein the grain is rye or oat, wherein the dried material has a particle size with a d$_{50}$ between 0.01 mm and 3 mm, and wherein the feed material has a moisture content between 2 wt % and 8 wt %.

* * * * *